US011891599B2

United States Patent
Patel et al.

(10) Patent No.: US 11,891,599 B2
(45) Date of Patent: Feb. 6, 2024

(54) RECOVERY OF NUCLEIC ACIDS FROM SOLID SUPPORTS

(71) Applicant: QIAGEN Healthcare Biotechnologies Systems GmbH, Hilden (DE)

(72) Inventors: Paresh Lakhubhai Patel, Cardiff South Glamorgan (GB); Lin Chen, ShangHai (CN); Melissa Schwandt, Lafayette, CO (US); Koya Reams, Silver Spring, MD (US); Thomas Hansen, Silver Spring, MD (US)

(73) Assignee: QIAGEN Healthcare Biotechnologies Systems GmbH, Hilden (DE)

( * ) Notice: Subject to any disclaimer, the term of this patent is extended or adjusted under 35 U.S.C. 154(b) by 0 days.

(21) Appl. No.: 16/615,645

(22) PCT Filed: May 18, 2018

(86) PCT No.: PCT/EP2018/063234
§ 371 (c)(1),
(2) Date: Nov. 21, 2019

(87) PCT Pub. No.: WO2018/215375
PCT Pub. Date: Nov. 29, 2018

(65) Prior Publication Data
US 2021/0214716 A1   Jul. 15, 2021

Related U.S. Application Data

(63) Continuation of application No. PCT/CN2017/085296, filed on May 22, 2017.
(Continued)

(51) Int. Cl.
*C12N 15/10* (2006.01)
*C12Q 1/6806* (2018.01)

(52) U.S. Cl.
CPC ....... *C12N 15/1006* (2013.01); *C12Q 1/6806* (2013.01)

(58) Field of Classification Search
CPC ............ C12N 15/1003; C12N 15/1006; C12N 15/1017; C12Q 1/6806; C12Q 1/686; B01L 3/50255; B01L 3/502707; B01L 3/502715
See application file for complete search history.

(56) References Cited

U.S. PATENT DOCUMENTS 5,342,931 A * 8/1994 Woodard ........... C12N 15/1006
536/25.4
5,447,864 A * 9/1995 Raybuck ............ C12N 15/1017
435/270
(Continued)

FOREIGN PATENT DOCUMENTS

EP        1641944 B1 *  6/2011  ......... C12N 15/1006
WO    WO 00/70041 A1    11/2000
WO    WO-2016106113 A1 *  6/2016  ........... C12Q 1/6844

OTHER PUBLICATIONS

Coyne et al. "Comparative Analysis of the Schleicher and Schuell IsoCode Stix DNA Isolation Device and the Qiagen QIAamp DNA Mini Kit", Oct. 2004, Journal of Clinical Microbiology, 42, 10, pp. 4859-4862. (Year: 2004).*
(Continued)

*Primary Examiner* — Samuel C Woolwine
(74) *Attorney, Agent, or Firm* — MEDLER FERRO WOODHOUSE & MILLS PLLC (57) ABSTRACT

Disclosed is a method for the recovery of nucleic acids from a solid support, the method comprising the steps, in any suitable order, of: a) providing a solid support at least a region of which is absorbent and impregnated with a chaotropic agent; b) combining a biological sample, possibly including nucleic acids, with the region; c) washing the region in a washing buffer solution; d) simultaneously heating and agitating the region in a further buffer solution; e) separating the region from the further buffer solution; f)
(Continued)

extracting at least a portion of any remaining further buffer solution from the region to provide an extracted buffer solution; g) combining the further buffer solution and the extracted buffer solution portion; and h) subsequently processing the combined buffer solutions in order to amplify any nucleic acids in said combined solution. Hardware suitable for implementing the above method and a kit of parts is disclosed also.

18 Claims, 4 Drawing Sheets

Related U.S. Application Data (60) Provisional application No. 62/536,031, filed on Jul. 24, 2017.

(56) References Cited

U.S. PATENT DOCUMENTS

| | | | |
|---|---|---|---|
| 6,168,922 B1 | 1/2001 | Harvey et al. | |
| 6,673,631 B1* | 1/2004 | Tereba | C12N 15/1013 436/526 |
| 2002/0090635 A1* | 7/2002 | Xia | C12N 15/1017 435/6.12 |
| 2003/0124651 A1* | 7/2003 | Pasupuleti | C12Q 1/706 435/69.1 |
| 2004/0019196 A1 | 1/2004 | Jackson et al. | |
| 2004/0023207 A1* | 2/2004 | Polansky | A61K 48/005 435/456 |
| 2006/0057738 A1* | 3/2006 | Hall | G01N 1/38 436/177 |
| 2009/0043087 A1* | 2/2009 | Davis | C12N 15/1017 536/55.3 |
| 2009/0048439 A1* | 2/2009 | Weisburg | C12N 15/1006 536/25.41 |
| 2011/0054157 A1* | 3/2011 | Bitner | C12N 15/1017 536/23.1 |
| 2011/0071031 A1* | 3/2011 | Khripin | C12N 15/101 506/7 |
| 2017/0306404 A1* | 10/2017 | Baird | C12Q 1/6874 |

OTHER PUBLICATIONS

Barbosa et al. "Chapter 7—DNA extraction: finding the most suitable method", 2016, Eds: Cook et al., Molecular Microbial Diagnostic Methods, Academic Press, pp. 135-154. (Year: 2016).*

Kwara. Eluting Genomic DNA from FTA Cards Using Heat pH Treatment. Apr. 12, 2007. Retrieved from: https://studylib.net/doc/7648445/dna-extraction-from-fta-cards. (Year: 2007).*

Thurn. RNA Extraction From Nasal Washes. Apr. 25, 2011. Retrieved from: http://www.bowdish.ca/lab/wp-content/uploads/2011/07/RNA_extraction-nasopharnyx.pdf. (Year: 2011).*

Eppendorf AG, Eppendorf ThermoMixer (R) F0.5/F1.5/F2.0/FP. 2018. Retrieved from: https://www.eppendorf.com/product-media/doc/en/104346/Eppendorf_Sample-Preparation_Operating-manual_ThermoMixer-F05-F15-F20-FP.pdf (Year: 2018).*

Qiagen, Investigator® Lyse&Spin Basket Kit Handbook. Nov. 2016. Retrieved https://www.qiagen.com/cn/resources/download.aspx?id=3850f41c-fec4-464a-8044-3211268c435b&lang=en. (Year: 2016).*

Li et al. An optimization method for elution of enteroviral RNA from a cellulose-based substrate. Journal of Virological Methods 186: 62-67. (Year: 2012).*

Mas et al. DNA Cards: Determinants of DNA Yield and Quality in Collecting Genetic Samples for Pharmacogenetic Studies. Basic & Clinical Pharmacology & Toxicology 101:132-137. (Year: 2007).*

VWR bioMarke, Issue 4 (44 pages). (Year: 2003).*

Thermo Scientific PCR and qPCR product guide (cover and p. 77). (Year: 2012).*

Microcon Centrifugal Filter Devices User Guide. (Year: 2005).*

Reid et al. Detailed phylogenetic analysis of primate T-lymphotropic virus type 1 (PTLV-1) sequences from orangutans (Pongo pygmaeus) reveals new insights into the evolutionary history of PTLV-1 in Asia. Infection, Genetics and Evolution 43:434-450. (Year: 2016).*

GE Healthcare Life Sciences: "Whatman FTA Elute," May 2011, Retrieved from the Internet: URL: https://www.gelifesciences.co.jp/catalog/pdf/WhatmanFTAElutedatafile_28984402AA.pdf.

De Vargas Wolfgramm et al., "Simplified buccal DNA extraction with FTA® Elute Cards," Forensic Science Int.: Genetics 3:125-127 (2009).

The International Search Report issued in International Application No. PCT/EP2018/063234, dated Jul. 6, 2018.

* cited by examiner

RECOVERY OF NUCLEIC ACIDS FROM SOLID SUPPORTS

TECHNICAL FIELD

The present invention relates to devices and methods for the improved recovery and processing of nucleic acids, such as DNA or RNA, from their solid supports such as treated cellulous fibre papers branded as FTA Elute™.

BACKGROUND

Nucleic acids, such as deoxyribonucleic acids (DNA) or ribonucleic acids (RNA), have become of increasing interest as analytes for clinical or forensic uses. Powerful new molecular biology technologies enable one to detect for congenital diseases or infectious diseases. These same technologies can characterize DNA for use in settling factual issues in legal proceedings such as paternity suits and criminal prosecutions. Nucleic acid testing has been made possible due to powerful amplification methods. One can take small amounts of nucleic acids which, in and of themselves would be undetectable, and increase or amplify the amount to a degree where useful amounts are present for detection.

The most commonly employed amplification technique is known as polymerase chain reaction, (PCR). Nucleic acid polymerases are used with template DNA from the sample in a cycled manner to create greater amounts of a starting nucleic acid materials, which are easily detected. One of ordinary skill in the art knows that the effectiveness and reproducibility of PCR amplification is dependent, in part, on the purity and amount of the DNA template. Certain molecules present in biological sources of nucleic acids are known to stop or inhibit PCR amplification. For example, in whole blood, hemoglobin is known to inhibit PCR reactions. Thus, the removal or inactivation of such inhibitors is a key factor in performing PCR reactions.

A method for storing DNA is disclosed in U.S. Pat. No. 5,496,562 to Leigh A. Burgoyne. An absorbent cellulose based matrix is treated with a combination of a weak base, a chelating agent, an anionic detergent, and, optionally, uric acid. The resulting product has an alkaline pH. DNA binds to this matrix and is protected against degradation.

A process for isolating nucleic acids is shown in U.S. Pat. No. 5,234,809 to William R. Boom et alia, (Boom). Recognizing that typical biological sources of nucleic acids can affect PCR reactions, Boom discloses using a combination of a biological source material, chaotropic salt, and a solid support, preferably finely divided glass. All three elements are combined in a liquid mixing device, with any nucleic acids present binding to the glass. After mixing, the solid support must be removed from the mixing device, washed, and the template nucleic acid eluted. Only then can it be exposed to amplification reactions.

Chaotropic salts have been used in association with isolating RNA. U.S. Pat. No. 4,483,920 to David Gillespie et alia, discloses a method for immobilizing messenger RNA onto filter material. Cellular components are solubilized using a chaotropic salt. The solubilized components are then passed through a filter, the messenger RNA selectively binding to the filter. The filter and RNA are baked prior to measurement by a labeled probe. Another method is shown by David Gillespie et alia, in U.S. Pat. No. 5,155,018. Here, RNA-containing sources are contacted with finely-divided glass in the presence of a binding solution comprising concentrated, acidified chaotropic salts. Under these conditions, RNA, but not DNA, binds selectively to the glass.

A poster disclosure at the annual American Association of Clinical Chemistry in 1995 by Dr. Michael A. Harvey et alia revealed that chaotropic salts can be used to prepare DNA from dried and untreated whole blood spots for PCR amplification. Hemoglobin present in dried untreated whole blood spots was known to cause an inhibition of PCR reactions. A cellulosic paper treated with a chaotropic salt was found to overcome the problem of hemoglobin inhibition in untreated whole blood spots.

FTA Elute and similar solid supports are treated with a chaotropic salt intended to preserve nucleic acids when dried on such supports having been deposited thereon usually as fluid samples, for subsequent genetic characterization, primarily by conventional amplification methods as PCR. Those supports can be used in a known protocol to collect, store, or purify nucleic acids either from a biological source, for example a biological source having naturally occurring nucleic acid amplification inhibitors present, (including either a buccal swab, cerebrospinal fluid, feces, lymphatic fluid, a plasma sample, a saliva sample, a serum sample, urine, or a suspension of cells or viruses), or from a treated whole blood biological source that has naturally occurring nucleic acid amplification inhibitors present, as well as added blood stabilization components that also inhibit nucleic acid amplification. More importantly, these nucleic acids can be released after collection or storage in a manner that enables them to be amplified by PCR. In particular, the solid supports comprise an absorbent material that does not bind nucleic acids irreversibly, and is impregnated with the chaotropic salt. A biological source sample is contacted with the impregnated absorbent material. Any nucleic acids present in the biological source can be either eluted or resolubilized off the absorbent material.

U.S. Pat. No. 6,168,922 to Michael Harvey et alia (incorporated herein by reference), describes certain embodiments of said FTA Elute and wherein it is disclosed that an absorbent material such as cellulosics, porous glasses and woven/non-woven porous polymers, can be impregnated with a chaotropic salt, to provide a releasable support for amplifiable nucleic acids, even in the presence of naturally occurring amplification inhibitors. In more detail the disclosure describes techniques to collect, store, or purify nucleic acids either from a biological source other than untreated whole blood, the biological source having naturally occurring nucleic acid amplification inhibitors present other than hemoglobin, (including samples from either a buccal swab, cerebrospinal fluid, feces, lymphatic fluid, a plasma sample, a saliva sample, a serum sample, urine, or a suspension of cells or viruses) or from a treated whole blood source that has naturally occurring nucleic acid amplification inhibitors present, as well as added blood stabilization components that also inhibit nucleic acid amplification. It is proposed that the absorbent treated material disclosed can be used to detect pathogens such as bacteria or viruses that can be found in the circulatory system. More importantly, these nucleic acids can be released after collection or storage in a manner that enables them to be amplified by conventional techniques such as PCR either by elution or re-solubilisation off the absorbent material. The device described can collect nucleic acids not only from point sources such as humans or animals, but also can be used to collect widely disseminated sources such as fungal spores, viruses, or bacterial spores, or biological material, such as bodily fluids, present at crime scenes.

A commercially known protocol for recovering nucleic acids from whole blood using sample collection papers provides for:
1. Blood sample collection on a sample collection paper.
3. Dry thoroughly.
3. Punch out a 3 mm sample with a sterile punch and place into a sterile micro-centrifuge tube.
4. Rinse punch in 500 µl of dH2 O by vortexing 3 times for 5 seconds.
5. Using a sterile pipette, remove water; centrifuge 5 seconds; pipette off excess.
6. Add 50 µl sterile water; heat to 95° C. for 30 minutes.
7. Remove the sample from the heater block and pulse vortex or gently tap the sample approximately 60 times.
8. Centrifuge whole mix for 30 seconds to separate the heavier eluate components from the punch.
9. Remove the punch using a sterile pipette tip and discard.
10. Add 5-10 µl eluate template to PCR reaction mixture.

That protocol gives good recovery rates for a majority of instances where biological sample collection and storage is required. However, in some instances, amounts of nucleic acids can be so small that the rinsing and dilution steps mentioned above risk losing what little nucleic acid there is in a sample and so the inventors have recognized that for samples that contain little nucleic acid material, improved recovery rates are required, and have devised an improved protocol for the recovery of that nucleic acid. That problem is typically encountered in attempting to extract DNA from solid supports used to collect forensic evidence. The inventors have further recognized that even small changes to existing protocols can differentiate successful from unsuccessful extractions.

DISCLOSURE OF THE INVENTION

The present invention provides a method for the recovery of nucleic acids from a solid support, the 5 method comprising the steps, in any suitable order, of:
a) providing a solid support at least a region of which is absorbent and impregnated with a chaotropic agent;
b) combining a biological sample, possibly including nucleic acids, with the region;
c) washing the region in a washing buffer solution;
d) simultaneously heating and agitating the region in a further buffer solution;
e) separating the region from the further buffer solution;
f) extracting at least a portion of any remaining further buffer solution from the region to provide an extracted buffer solution;
g) combining the further buffer solution and the extracted buffer solution portion; and
h) subsequently processing the combined buffer solutions in order to amplify any nucleic acids in said combined solution.

In embodiments, any one or more of the following refinements may be employed in the method above:

The solid support may be a sheet of absorbent material, for example as sold under the brand name FTA Elute sample collection paper, onto which a sample is deposited during sample collection, and from which said region is removed, with a core punch or the like, optionally after drying the sample and solid support. Alternatively, the solid support may be pre-formed into a plurality of said regions, for example retained in a well where the sample is also deposited, and one or more of said regions can be processed simultaneously according to the method above. The chaotropic agent may be one or more of guanidinium salts such as guanidine isothiocyanate, guanidine thiocyanate, guanidine hydrochloride, sodium iodide, sodium perchlorate, potassium iodide, sodium (iso)thiocyanate, urea, or combinations thereof. Other chaotropic agents could be used as described herein.

Said washing buffer may be an alkaline solution, for example a TE buffer which includes TRIS (hydroxymethylaminomethane) and EDTA (ethylenediaminetetraacetic acid), or other aminopolycarboxylic acid in solution with distilled water. Preferably the washing buffer is a TE-4 buffer solution. The washing is preferably performed without agitating the region, and is preferably performed at room temperature. The washing step is preferably performed 3 times, and after each washing step the washing buffer may be removed and discarded.

Once washed, the region may be processed further by said heating and agitating step submerged in a further buffer solution, which solution may have the same composition as the washing solution, for example the further buffer solution may be TE-4 buffer solution. Heating is preferably at a temperature of 95 degrees Celsius for about 30 minutes e.g. 20 to 40 minutes, with a slight agitation so as inhibit the disassociation of poly or oligo-molecules which form the nucleic acids. An agitation of about 1000 cycles per minute is preferred i.e. about 300 to 1500 cycles per minute of a cyclic mechanism also known as a shaker, for the same or a similar length of time as the heating.

Preferably the separating of the region from the further buffer solution is performed by placing the region in a basket or cage above the remaining further buffer solution. However, that step could equally usefully be performed by lifting a basket or cage out of the further buffer solution, where the basket or cage already contains the already heated/agitated region.

Preferably said extracting of a majority of the remaining buffer solution still held in the absorbent material of the region can be removed by spinning the region, for example in the basket or cage mentioned above thus employing centripetal force to extract buffer solution from the region, or by fluid pressure, for example a higher air pressure on one side of the region compared to the air pressure on an opposing side of the region, in each case causing buffer solution to be removed from the absorbent material. That extracted solution will enable the recovery of a greater proportion of any nucleic acids still present on the region following the heating and agitation step mentioned above. Whilst conventional single spin baskets and centrifuges could be employed for this step, other apparatus described herein could be used also.

Preferably the combining of the further buffer and the extracted buffer takes place in a well under the spin basket or otherwise arranged to hold the further buffer solution and also to catch the extracted buffer solution.

Preferred techniques for subsequent processing of the combined solutions (the further buffer solution and any extracted buffer solution) are described below.

It can be seen that the above steps simplify the processing of biological samples, and include an extracting step, which in one embodiment can be accomplished by spinning the solid support region in a spin cage or the like to drive off eluate into a small volume of buffer solution or directly into the separated further buffer solution. In that way, even small quantities of nucleic acids otherwise still bound to the solid support are urged off the region for subsequent processing such as DNA PCR amplification. More advantages and benefits of the present invention will become readily apparent to the person skilled in the art in view of the detailed description below, the drawings and the claims herein, where it is envisaged that any features mentioned or illustrated may be combined with any other features without generalising the invention or adding to its content.

DESCRIPTION

The method described herein provides effective recovery of extracted DNA stored on Whatman™ FTA™ Elute Cards or the like. A dilution series of DNA extracts were prepared and applied to FTA Elute cards. The data collected demonstrates that complete STR profiles can be obtained from DNA extracts with starting concentrations as low as 50 pg/μl.

FTA Elute contains a chaotropic salt and with sample application, proteins remain tightly bound while DNA is eluted from the matrix. The eluted DNA then can be used for real-time PCR, STR analysis (standard amplification) and sequencing applications. Forensic laboratories can process thousands of DNA samples a year. The extracted DNA from these samples is routinely stored frozen in micro-centrifuge tubes to archive the samples for potential future testing. For many laboratories, DNA extract storage in freezers has become increasingly costly. This application note examines the use of FTA Elute cards for room temperature storage of extracted DNA.

FTA Elute cards are used for collecting, purifying, and storing nucleic acids from biological sources comprises an absorbent material that does not bind to nucleic acids and a chaotropic agent impregnated about the absorbent material. (For the purposes of the present invention, "chaotropic agent" include any substance capable of altering the secondary, tertiary, or quaternary structure of biomolecules in aqueous solution, but leaves the primary structure intact.) Preferably, a chaotropic agent should inactivate any nucleic acid amplification inhibitors present in the biological source, by precipitation, by inducing the inhibitor to irreversibly bind to the matrix, or by causing substantially irreversible denaturation of the inhibitor. Suitable chaotropic agents include guanidinium salts such as guanidine isothiocyanate, guanidine thiocyanate, guanidine hydrochloride, sodium iodide, sodium perchlorate, potassium iodide, sodium (iso) thiocyanate, urea, or combinations thereof. Other chaotropic agents could be used, such as: n-Butanol; Ethanol; Guanidinium chloride; Lithium perchlorate; Lithium acetate; Magnesium chloride; Phenol 2-propanol; Sodium dodecyl sulfate; and Thiourea, or combinations thereof. The agents can be impregnated about the absorbent material by contacting the absorbent material with a solution containing the chaotropic agent for example containing from about 0.1M to 6.0M concentrations, preferably 0.5M to 2.0M. The absorbent material is then dried.

Many materials are suitable as the absorbent material. The main characteristics needed for the absorbent material are that it is or can be made hydrophilic, and does not substantially bind nucleic acids irreversibly through either hydrophobic, ionic, covalent, or electrostatic means. The matrix must not by itself inhibit or bind amplification reactants, release substances that effect amplification reactants or otherwise affect PCR and other amplification reactions. Suitable materials include cellulosics, woven porous polymers, or non-woven porous polymers, including polyesters and polypropylenes.

Common inhibitors to nucleic acid amplification can be present naturally in a biological source or can be added for handling or processing of a sample from a biological source, (Gunnar Tasa et alia, 1995, Methods in Molecular and Cellular Biology; 5, 122-124). Naturally occurring chelating molecules, enzymes and proteins can damage either nucleic acid templates, (such as RNAses, DNAses), or damage PCR polymerases used in the amplification reactions, (such as proteases). These substances can be found in buccal swabs, cerebrospinal fluids, feces, lymphatic fluids, plasma, saliva, serum, sputum, or urine. In addition, components added to whole blood samples can interfere with nucleic acid amplification reactions. Examples of such components used to treat whole blood include anticoagulants, such as heparin, or chelators, such as EDTA or citrate anion.

EXAMPLE

Blood:

Human Blood from an anonymous individual was collected through venipuncture into a blood collection tube containing dipotassium EDTA. For this example 4 replicates of 200 μl of the whole human blood were obtained. The DNA was then extracted using the MagJET™ Whole Blood Genomic DNA Purification Kit (ThermoFisher Scientific) following the manufacturers protocols. Each DNA sample was eluted into 150 μl of elution buffer included in the kit. The DNA extracts were then combined for a total volume of 600 μL. The combined extract was quantified using a NanoDrop™ 2000 UV-Vis Spectrophotometer (Thermo Scientific).

Figure 1A:
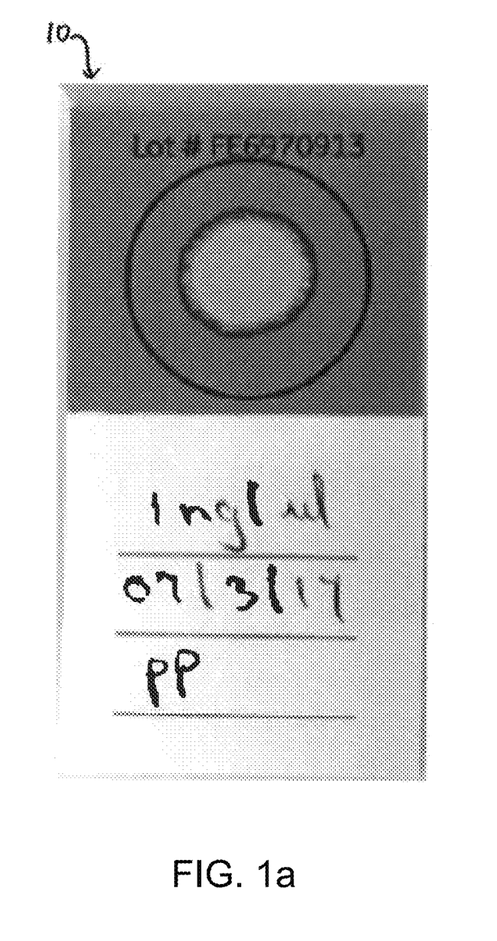
FIGS. 1a and 1b show images of a solid support for use with the invention.
Figure 1B:
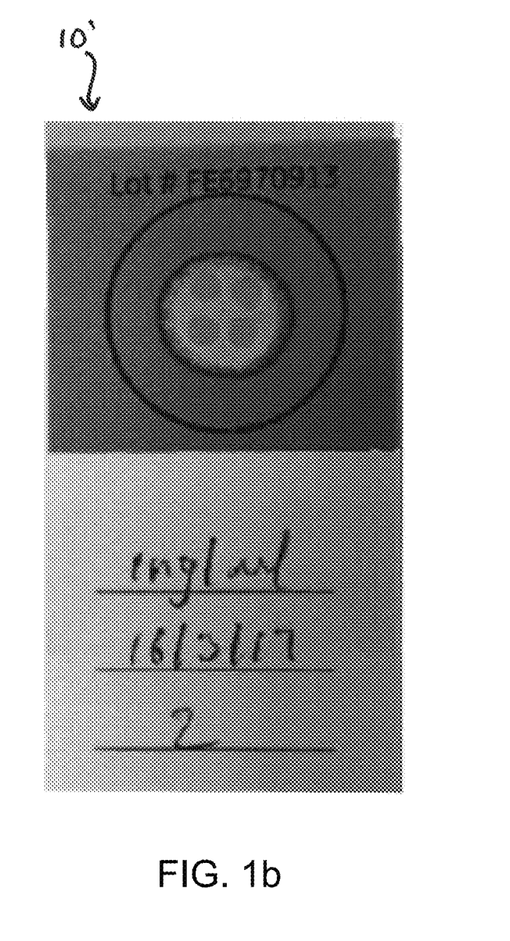

Several dilutions of the extracted DNA were prepared by diluting the original extract with TE-4 buffer (10 mM Tris-HCl, 0.1 mM EDTA) in a series including 10 ng/μl, 1 ng/μl, 500 pg/μl, 100 pg/μl, and 50 pg/μl of the extracted DNA. Five Indicating FTA Elute Micro Cards were spotted with 25 μl of each dilution and allowed to dry at room temperature for at least 3 hours. An example of the spotted FTA Elute card 10 is shown in FIG. 1a. Punches (4×3 mm) were removed from within the sample-containing area of each FTA Elute card. An example of the card 10' which has the punches removed is shown in FIG. 1b. Multiple punches were used to provide a representative sampling from each card. The four punches from each card were placed in a 1.5 ml microcentrifuge tube and washed 3 times with 500 μl of TE-4 buffer. One hundred fifty microliters (150 μl) of TE-4 buffer was then added to each set of punches. The samples were incubated on an Eppendorf Thermomixer at 95° C. for 30 min at 1000 rpm which provides a controlled gentle circular mixing movement. The punches and eluate were transferred to DNA IQ™ Spin Baskets (Promega catalog #V1225) and centrifuged at maximum speed about 10,000 rpm for 2 minutes. Assuming each punch weighs about 1 gram then a conventional centrifuge of radius 10 cm and angular velocity of 10,000 rpm will provide about 100 N extraction force on each of the punches. The spin baskets were removed, the punches discarded, and the eluate taken forward for downstream processing.

In order to show the results obtained the DNA concentration of the original dilution series and the DNA yield from the samples were measured using quantitative PCR (qPCR) and an ABI™ 7900HT Fast Real-Time PCR System (Thermo Fisher Scientific). Reactions were prepared using the Quantifiler™ Human DNA Quantification Kit (4343895, Thermo Fisher Scientific).

All samples, except for 10 ng/µl samples, were concentrated using Microcon® DNA Fast Flow Devices (Cat #MRCFOR100) to concentrate samples from 150 µl to a smaller volume to allow sufficient DNA to be placed into STR amplification reactions. One hundred fifty microliters (150 µl) of each extract was placed in the Microcon for concentration. The final volume of concentrated DNA extract was measured using a pipette. The final concentrated sample volume and initial concentration of the extracts were used to estimate the concentration of the extract. That value was used for determination of the volume of sample to be used for STR amplification.

Samples were amplified using the PowerPlex® Fusion System (Promega) at 30 cycles on a 9700 thermal cycler (Thermo Fisher Scientific). Based on the manufacturer's recommendation, the target DNA input was 0.5 ng. STR fragments were separated on a 3500xL Genetic Analyzer (ThermoFisher Scientific) and the data was analyzed in GeneMapper™ ID-X v1.5 software (ThermoFisher Scientific).

Each FTA Elute card was spotted with 25 µl of DNA extract. As shown in FIG. 1b, four 3 mm punches were removed from each card. The average diameter of a 25 µl stain was 10 mm. Based on this diameter, the area of a 25 µl stain of DNA extract about 100-150 mm². The total calculated area of four 3 mm punches is equivalent about 25-30 mm². The four 3 mm punches are approximately 25% of the total stained area and are expected to contain 25% of the DNA placed on the card. These calculations were used to determine the percentage of DNA recovered from the FTA Elute cards for each concentration of DNA in the dilution series.

Figure 2:
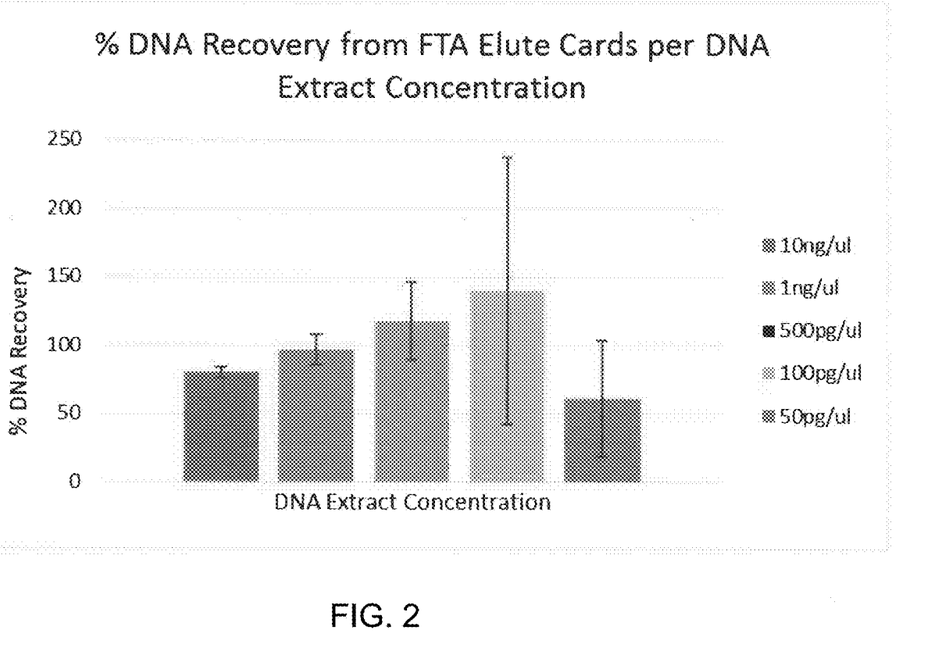
FIG. 2 is a graphical representation of the effectiveness of the method of the invention described herein.

The concentrations of DNA Extract applied to the FTA Elute cards were 10 ng/µl, 1 ng/µl, 500 pg/µl, 100 pg/µl, and 50 pg/µl and were verified using the Quantifiler® Human DNA Quantification Kit. The DNA average recovery obtained from each DNA extract concentration was 80%, 97%, 118%, 140% and 62%, respectively (see FIG. 2). There was large variability in the quantification values for the 50 pg/µl and 100 pg/µl samples with the values near the limit of detection.

Following Microcon™ concentration, the samples were amplified with the PowerPlex® Fusion System. Some samples did not yield enough DNA to reach the targeted amount of 0.50 ng, in which case the entire volume of sample was amplified. The minimum amount of DNA placed in the amplification reaction, based on calculations, was 0.2 ng. The data illustrates that a complete STR DNA profile was obtained from all samples with starting concentrations ranging from 10 ng/µl down to 50 pg/µl (see FIG. 2).

This example demonstrates that FTA Elute cards serve as a novel room temperature storage solution for DNA extracts obtained from forensic samples. Sample extracts containing as little as 50 pg/µl, stored on FTA Elute cards, were of sufficient quality and quantity to develop full STR profiles following elution.

One preferred nucleic acid recovery protocol according to the invention is recited below:

Materials Required:
Indicating FTA Elute Micro Card (catalog #WB120412 or WB120411)
Low TE Buffer e.g. TE-4 buffer (10 mM Tris-HCl, 0.1 mM EDTA)
Nuclease-free water
3 mm diameter puncher
Cutting Mat
Thermomixer
1.5 ml Micro Tubes
Spin baskets Protocol:
Label the FTA card with the appropriate sample identification.
Pipette 25 µl of thawed DNA Extract to the center of the Indicating FTA Elute Micro card.
Allow the sample to air dry 2-3 hours at room temperature.
Once completely dried, store the samples in a cool and dry environment until ready to use.

Recovery:
1. To prevent carry-over between samples, always ensure that the sample applied is dry before taking a punch.
2. Place the sample-containing FTA Elute card on a cutting mat.
3. Remove four 3 mm punches from the FTA Elute card and place the punches into a single 1.5 ml micro tube.
4. To clean the punching device in between samples, remove one punch from a blank unused FTA Elute card and discard the punch in the appropriate receptacle.
5. Repeat steps 3 and 4 for each of the remaining samples.
6. Pipette 500 µl of low TE buffer into each tube containing the 3 mm punches.
7. Close the tube and mix the contents of the micro tube for 5 seconds.
8. Remove and discard the low TE buffer supernatant.
9. Repeat steps 6-8 (for a total of three washes with low TE buffer).
10 Pipette 150 µl of low TE buffer to the micro tube(s) containing sample punches.
11. Place the tube(s) on a thermomixer at 95° C. for 30 minutes at 1000 rpm.
12. After that incubation, transfer the samples to spin baskets and spin at maximum speed for 2 minutes.
13. Combine the resultant buffer from step 11 with the buffer extracted from the punch(es) resulting from step 12.
14. Remove the spin baskets and store the combined extracts at 4° C. for short term or −20° C. for long term storage.

Figure 3:
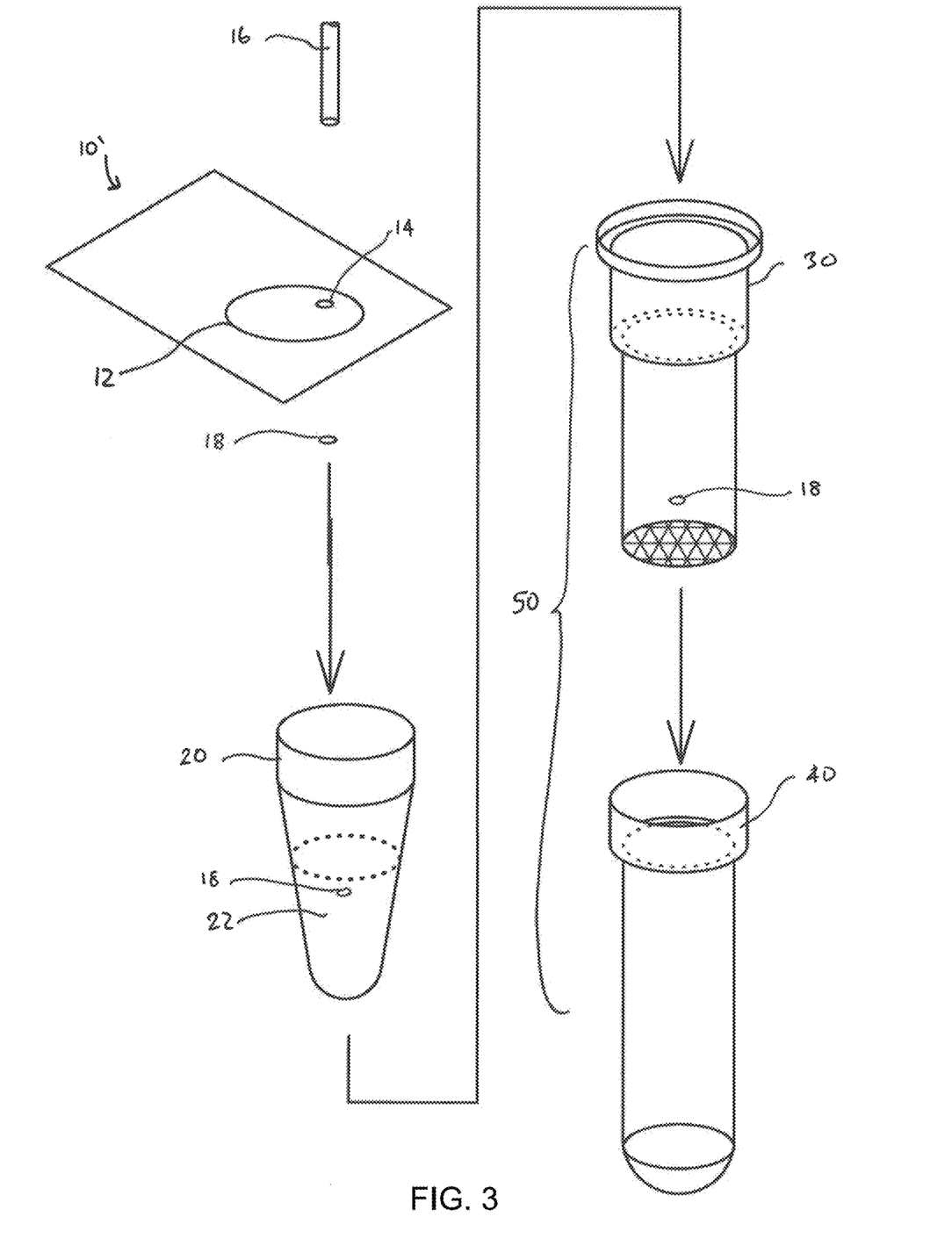
FIG. 3 is a schematic representation of hardware for use with the invention.

Hardware useable in the process mention immediately above is illustrated in FIG. 3. A labelled FTA Elute card 10' has a biological sample deposited thereon at a region 12 where it is absorbent. In this case the card 10' has been previously dried and stored. A portion 14 of that region 12 can be cut from the remainder using a puncher 16, to form a disk of material 18 known as a punch. That punch 18 can be dropped into a processing well 20 and a washing solution 22 can be added to the well 20 as described above. A conventional agitator can be used to circulate the washing solution for example containing Tris and EDTA, and the same washing steps can be performed a further time or a further two times, or multiple times dependent on the sample characteristics, each time with a fresh washing solution. After washing, further liquid (which can be the same solution as the washing solution) is added to the well 20, and that liquid together with the punch 18 is heated to around 95° C. for 30 minutes in a conventional thermocycler while agitating the well 20 at around 1000 cycles per minute. The punch 18 is then removed from the well and deposited into the cage 30 of a spin cage assembly 50, which includes the cage 30 and a liquid capture well 40. The assembly 50 can be spun at 10,000-15,000 rpm briefly to remove any remining liquids in the punch 18. The heated liquid from the well 20 and the extracted liquid from the liquid capture well 40 are combined and can be stored at 4° C. for short term or −20° C. for longer term storage.

Figure 4A:
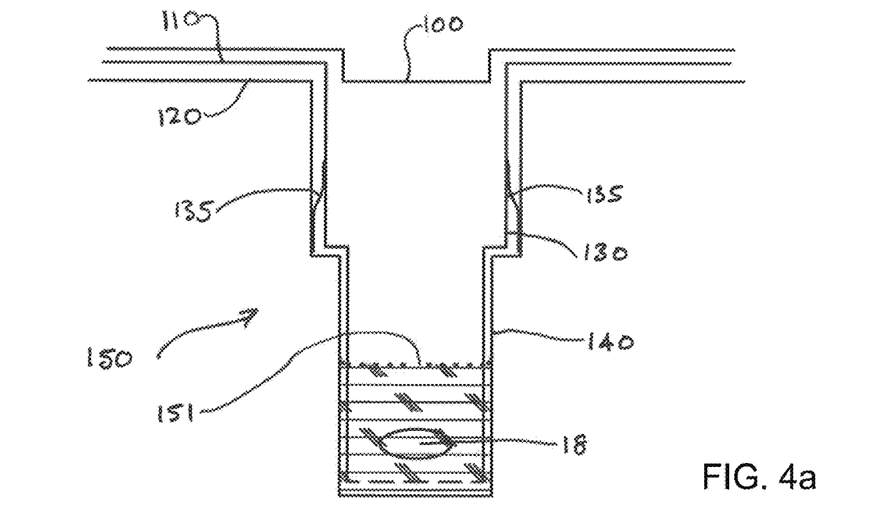
FIGS. 4a, b and c show further hardware for use with the invention.
Figures 4B, 4C:
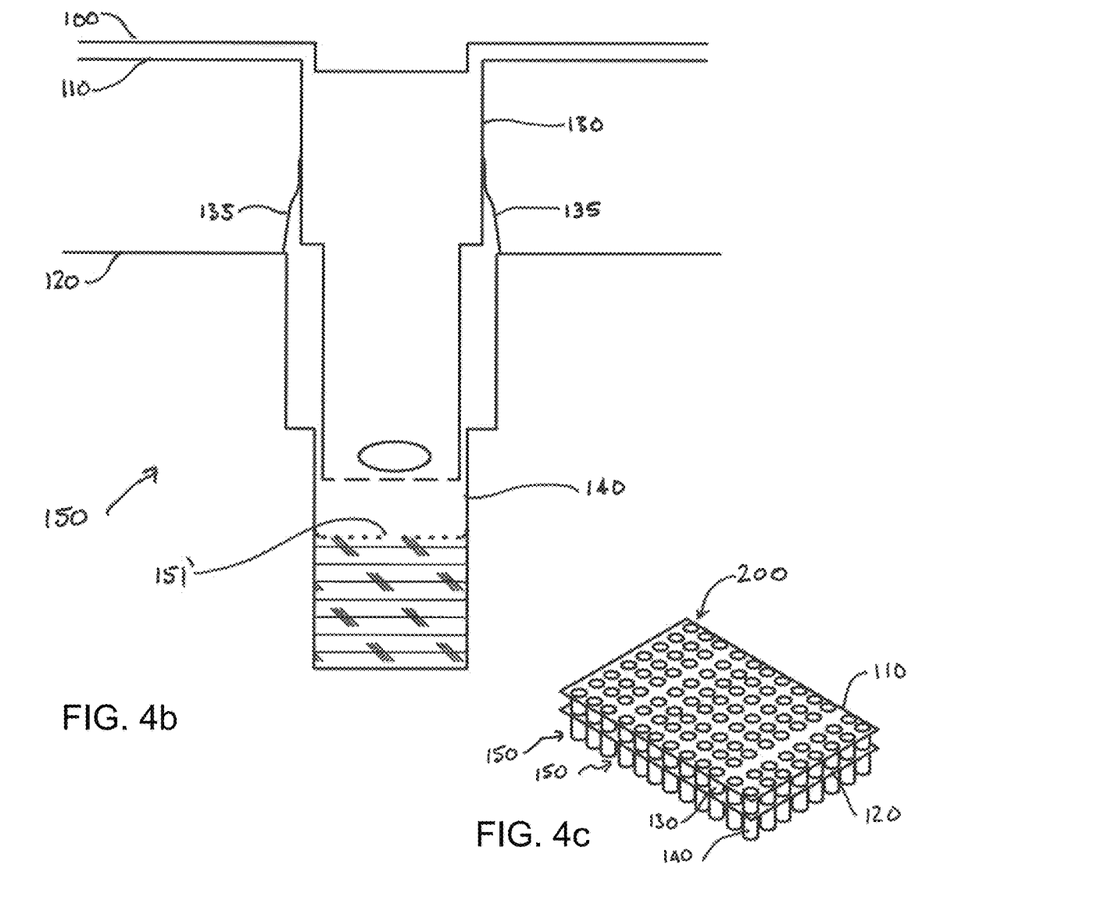

A modification of the hardware shown in FIG. 3 is illustrated in FIGS. 4a,b and c. In FIG. 4a, a section through a processing well 150 is shown, which can be one of a number of adjacent similar wells formed in well holder plates 110 and 120 , which are each formed with plural nesting features of a cage 130 inside a combined processing and liquid capture well 140, as well as a lid plate 100. Although such wells 150 may be used individually, a two dimensional array of such wells could be used, for example a 96 (8 by 12) well array 200 could be used, as shown in FIG. 4c, each cage 130 and well 140 being respectively interconnected by the well holder plates 110 and 120.

In use, steps 1 to 10 of the method above can be conducted using sample-containing regions 18 placed in the well 150 shown in FIG. 4a. Liquid buffer, for example at a level 151 can be introduced into the well 150 when the lid 100 is removed. However, rather than transferring the sample 18 into a spin basket assembly 50 or the like, the cage 130 can be raised out of the residual buffer liquid for the spinning step, to a position shown in FIG. 4b. At that time, spring clips 135 will spring outwardly and prevent the cage 130 from returning below the new liquid level 151' during spinning. That spinning step can be done using the 2D array 200 shown in FIG. 4c, which is shown ready to be spun, i.e. is shown with its wells in the configuration also shown in FIG. 4b with spring clips 135 deployed to prevent the cages from being pushed into the wells 140. The cage 130 (singular or as an array) can be withdrawn after spinning and the lid 100 replaced for longer term storage of the DNA etc containing liquid in the wells 140 prior to amplification by known techniques.

Since the above-mentioned hardware 200 is readily useable in an automated process, the punches 18 may be pre-formed and inserted into the well 150, with a biological sample added to the punch after it has been placed in the well 150.

The skilled person will appreciate that the present invention can incorporate any combination of the preferred features described above. All publications or unpublished patent applications mentioned herein are hereby incorporated by reference thereto. Other embodiments of the present invention are not presented here which are obvious to those of ordinary skill in the art, now or during the term of any patent issuing from this patent specification, and thus, are within the spirit and scope of the present invention. The invention is not to be seen as limited by the embodiments described above, but can be varied within the scope of the appended claims as is readily apparent to the person skilled in the art, for example, the example given above requires drying of a sample on a solid support before processing. That drying is performed in the examples to show that drying is possible, but is not an essential step. However, in practice the drying allows long term storage, if needed, in place of conventional freezing. Thus, the combining of the sample with the solid support may be done prior to other steps which form this invention, for dry storage of the sample on the solid support, hours, days, weeks, months or years prior to the steps c) to h) defined in the claims which are used to recover nucleic acids present initially in the sample. Indefinite storage can be maintained in dry conditions, for example, by storing the sample-containing solid support in a sealed container along with desiccant material.

The invention claimed is:

1. A method for recovering nucleic acids from a solid support, the method comprising:
    (a) combining a biological sample with a region of a solid support, wherein the region is absorbent and impregnated with a chaotropic agent;
    (b) washing the region in a washing buffer solution, wherein the washing buffer solution is an alkaline solution;
    (c) simultaneously heating and agitating the region in a further alkaline buffer solution;
    (d) separating the region from the further alkaline buffer solution without centrifugation, wherein the separating of the region from the further alkaline buffer solution is performed by disposing the region in a porous container above the remaining further alkaline buffer solution;
    (e) extracting at least a portion of any remaining further alkaline buffer solution from the region to provide an extracted alkaline buffer solution, wherein the separating and the extracting are performed using different methods;
    (f) combining the further alkaline buffer solution from (d) and the extracted alkaline buffer solution portion; and
    (g) subsequently processing the combined buffer solutions in order to amplify any nucleic acids in said combined solution.

2. The method of claim 1, wherein the solid support is an absorbent sheet material onto which a sample is deposited and dried.

3. The method of claim 1, wherein said region is obtained by removing one or more pieces or punches of said solid support.

4. The method of claim 1, wherein the region is preformed into a plurality of said regions.

5. The method of claim 1, wherein the chaotropic agent is selected from a group consisting of guanidine isothiocyanate, guanidine thiocyanate, guanidine hydrochloride, sodium iodide, sodium perchlorate, potassium iodide, sodium (iso)thiocyanate, urea, and any combination thereof.

6. The method of claim 1, wherein the step a) of combining the biological sample with the region, further includes drying the combined sample and region, and optionally storing the dried combined sample and region for hours, days, weeks, months or years, prior to said washing step b).

7. The method of claim 1, wherein said washing buffer comprises TRIS (hydroxymethylaminomethane) and EDTA (ethylenediaminetetraacetic acid), or an aminopolycarboxylic acid in solution with distilled water.

8. The method of claim 7, wherein the washing buffer is a buffer solution comprising 10 mM Tris-HCl and 0.1 mM EDTA.

9. The method of claim 1, wherein the washing step b) is performed without substantial agitation of the region, and/or is performed more than once, and/or used washing buffer is removed between washes.

10. The method of claim 1, wherein said further alkaline buffer solution used in step c) has the same composition to the alkaline buffer solution used for said washing step b).

11. The method of claim 1, wherein said heating is at a further alkaline buffer solution temperature of 95 to 98 degrees Celsius for 20 to 40 minutes.

12. The method of claim 1, wherein said agitation is cyclic machine movements of 300 to 1500 cycles per minute for the same length of time as the heating.

13. The method of claim 1, wherein the porous container is a basket or cage.

14. The method of claim 13, wherein the separating of the region from the further alkaline buffer solution is performed by lifting the basket or cage.

15. The method of claim 14, wherein said extracting of a portion of the remaining buffer solution still held in the absorbent material of the region is implemented by spinning the region in the basket or cage causing buffer solution to be extracted from the absorbent material.

16. The method of claim 15, wherein the combining of the further alkaline buffer and the extracted alkaline buffer takes place in a well under the basket or cage.

17. Hardware suitable for carrying out the method according to claim 1, said hardware comprising a processing well, a porous container for holding said region(s), and a liquid capture well arranged for capture of liquid extracted from the region(s) during spinning, wherein said processing well and said liquid capture well are combined as one well, and wherein the porous container comprises spring clips allowing removal of the porous container from a first, more inserted position in the well to a second, less inserted position in the well, but hinders movement of the porous container from the second position in the well to the first position in the well.

18. The hardware of claim 17, wherein said porous container is a basket or cage.

\* \* \* \* \*